(12) United States Patent
Medo

(10) Patent No.: US 7,914,822 B2
(45) Date of Patent: Mar. 29, 2011

(54) METHOD OF PRODUCING NUTRITIONAL PRODUCTS FROM HUMAN MILK TISSUE AND COMPOSITIONS THEREOF

(75) Inventor: Elena Maria Medo, Murrieta, CA (US)

(73) Assignee: Prolacta Bioscience, Inc., Monrovia, CA (US)

( * ) Notice: Subject to any disclaimer, the term of this patent is extended or adjusted under 35 U.S.C. 154(b) by 107 days.

(21) Appl. No.: 12/372,376

(22) Filed: Feb. 17, 2009

(65) Prior Publication Data

US 2009/0258121 A1 Oct. 15, 2009

Related U.S. Application Data

(60) Division of application No. 11/012,611, filed on Dec. 14, 2004, now abandoned, which is a continuation of application No. 10/144,325, filed on May 13, 2002, now abandoned.

(60) Provisional application No. 60/290,823, filed on May 14, 2001.

(51) Int. Cl.
*A61K 35/20* (2006.01)

(52) U.S. Cl. ....................................... 424/535

(58) Field of Classification Search .................. None
See application file for complete search history.

(56) References Cited

U.S. PATENT DOCUMENTS

| | | | |
|---|---|---|---|
| 2,567,898 | A | 9/1951 | Staaff |
| 4,455,483 | A | 6/1984 | Schonhuber |
| 5,303,598 | A | 4/1994 | Binder |
| 5,334,822 | A | 8/1994 | Sanford |
| 5,505,955 | A | 4/1996 | Peterson et al. |
| 5,983,198 | A | 11/1999 | Mowery |
| 6,183,803 | B1 | 2/2001 | Morcol et al. |
| 6,194,009 | B1 | 2/2001 | Kamarel |
| 6,270,827 | B1 | 8/2001 | Gaull et al. |
| 6,294,206 | B1 | 9/2001 | Barrett-Reis et al. |
| 6,652,900 | B2 | 11/2003 | Lindquist |
| 6,780,987 | B1 | 8/2004 | Herman et al. |
| 2002/0155445 | A1 | 10/2002 | Jarvik |
| 2002/0182243 | A1 | 12/2002 | Medo |
| 2003/0093171 | A1 | 5/2003 | Soehnlen |
| 2003/0152942 | A1 | 8/2003 | Fors et al. |
| 2003/0219812 | A1 | 11/2003 | Quay et al. |
| 2004/0181205 | A1 | 9/2004 | Morton et al. |
| 2004/0265462 | A1 | 12/2004 | Carlson |
| 2005/0053707 | A1 | 3/2005 | Kopf et al. |
| 2005/0100634 | A1 | 5/2005 | Medo |
| 2006/0115558 | A1 | 6/2006 | Lamothe |
| 2006/0204632 | A1 | 9/2006 | Barrett-Reis et al. |
| 2006/0233915 | A1 | 10/2006 | Puski et al. |
| 2007/0098863 | A1 | 5/2007 | Medo et al. |
| 2007/0203802 | A1 | 8/2007 | Medo et al. |
| 2008/0118615 | A1 | 5/2008 | Hartmann et al. |
| 2008/0124430 | A1 | 5/2008 | Medo et al. |
| 2008/0227101 | A1 | 9/2008 | Medo et al. |

FOREIGN PATENT DOCUMENTS

| | | |
|---|---|---|
| WO | WO-00/43550 | 7/2000 |
| WO | WO/2007/035870 | 3/2007 |
| WO | WO-2008/027572 | 3/2008 |
| WO | WO-2008/067486 | 6/2008 |
| WO | WO-2008/073888 | 6/2008 |

OTHER PUBLICATIONS

Davies, D. P., "Adequacy of Expressed Breast Milk for Early Growth of Preterm Infants," Arch. Disease in Childhood. 1977. vol. 52, pp. 296-301.

Hagelberg S., et al., "Amino Acid Levels in the Critically Ill Preterm Infant Given Mother's Milk Fortified with Protein from Human or Cow's Milk" Acta Paediatr Scan.1990. vol. 79, pp. 1163-1174.

Hagelberg, S., et al., "The Protein Tolerance of Very Low Birth Weight Infants Fed Human Milk Protein Enriched Mothers' Milk" Acta Paediatr Scan. 1982. vol. 71, pp. 597-601.

Hylmo, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.

Lindblad B.S., et al., "Blood Levels of Critical Amino Acids in Very Low Birthweight Infants on a High Human Milk Protein Intake" Acta Paediatr Scan.1982.vol. 296, pp. 24-27.

Moro, G.E., et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 1991. vol. 13, pp. 150-154.

PCT/US07/85969 International Search Report and Written Opinion, May 8, 2008, Prolacta Bioscience, Inc., et al.

PCT/US07/86973 International Search Report and Written Opinion, Mar. 5, 2008, Prolacta Bioscience, Inc., et al.

PCT/US07/19234 International Search Report and Written Opinion, Jan. 18, 2008, Prolacta Bioscience, Inc., et al.

PCT/US06/36827 International Search Report and Written Opinion, Mar. 26, 2008, Prolacta Bioscience, Inc., et al.

Polberger, S.K.T., "Fortified Human Milk for Very Low Birth Weight Infants: Effects on Growth and Metabolism," Dept. Pediatrics, University of Lund, Malmo 1990, pp. 1-148.

Polberger, S.K.T., et al., "Amino Acid Concentrations in Plasma and Urine in Very Low Birth Weight Infants Fed Non-Protein-Enriched or Human Milk Protein-Enriched Human Milk," Department of Pediatrics, University of Lund, Malmö General Hospital, S-21401 Malmö Sweden, pp. 131-148. Pediatrics 1990; 86: 909-915.

(Continued)

*Primary Examiner* — Christina Bradley

(74) *Attorney, Agent, or Firm* — Cooley LLP

(57) ABSTRACT

Methods of isolating, treating, storing and processing human milk, as well as nutritional formulations of human milk comprising protective human milk proteins.

4 Claims, No Drawings

OTHER PUBLICATIONS

Polberger, S.K.T., et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.

Polberger, S.K.T., et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 1990; 79(8-9): 729-736.

Polberger, S.K.T., et al., "Growth of Very Low Birth Weight Infants on Varying Amounts of Human Milk Protein," Department of Pediatrics, University of Lund, Malmö General Hospital, S-21401 Malmö Sweden, pp. 69-87. Pediatr Res 1989; 25: 414-419.

Polberger, S.K.T., et al., "Urinary and Serum Urea as Indicators of Protein Metabolism in Very Low Birth Weight Infants Fed Varying Human Milk Protein Intakes," Department of Pediatrics, University of Lund, Malmö General Hospital, S-21401 Malmö Sweden, pp. 89-99. Acta Paediatr Scand. 1990; 79(8-9): 737-42.

Ronnholm, K., et al., "Supplementation with Human Milk Protein Improves Growth of Small Premature Infants Fed Human Milk," Pediatrics. 1986. vol. 77, No. 5, pp. 649-653.

Schanler, R., et al., "Enhanced Fecal Excretion of Seleted Immune Factors in Very Low Birth Weight Infants Fed Fortified Human Milk," Pediatric Research. 1986. vol. 20, No. 8, pp. 711-715.

Schanler, R., et al., "Fortified Mothers' Milk for Very Low Birth Weight Infants; Results of Growth and Nutrient Balance Studies," J. Pediatrics. 1985. vol. 107, No. 3, pp. 437-444.

Schanler, R., et al., "Fortified Mothers' Milk for Very Low Birth Weight Infants: Results in Macromineral Balance Studies," J. Pediatrics. 1985. vol. 107, No. 5, pp. 767-774.

Schanler, R., et al., "Mineral Balance Studies in Very Low Birth Weight Infants Fed Human Milk," J. Pediatrics. 1988: vol. 113, vol. 1, Part 2, pp. 230-238.

Srinivasan, L., et al., "Increased Osmolality of Breast Milk with Therapeutic Additives," Arch Dis Child Fetal Neonatal Ed. 2004. 89:F514-17.

Terpstra, et al., "Antimicrobial and Antiviral Effect of High-Temperature Short-Time (HTST) Pasteurization Applied to Human Milk," Breastfeeding Med. 2007. vol. 2, pp. 27-33.

Virus Safety Services, Sanquin Research, Final Report FR4500, "Process Validation Breast Milk Step 1 for Inactivation of BVDV/HAV/HIV/PSR," May 27, 2002. pp. 1-33.

Voyer, M., et al. "Human Milk Lacto-Engineering," Acta Paediatr Scan. 1984. vol. 73, pp. 302-306.

Arnold, "How North American Donor Banks Operate: Results of a Survey: Part 2," J. Hum. Lact., 13(3):243-46, Sep. 1997.

Bernsahw, N. J., "Milk Banking: an Idea That Has Come of Age. Non-Profit Milk Banking," Seminar delivered at Utah Breastfeeding Coalition Meeting, Aug. 29, 2006.

The Dairy Council, "The Nutritional Composition of Dairy Products," pp. 1-49, 2002.

Prentice, A., "Constituents of Human Milk," *Food and Nutrition Bulletin*, the United Nations University Press, 17(4), Dec. 1996.

Jenness and Palmer, "Substances Adsorved on the Fat Golbules in Cream and Their Relation to Churning. V. Composition of the 'Membrane' and Distribution of the Adsorbed Substances in Chuming," *J. Dairy Science* 28(8):611-623, 1945.

Jensen et al., "Lipids of Bovine and Human Milks: A Comparison," *J. Dairy Science* 73:223-40, 1990.

Krukovsky et al., "The Effects of Nordihydroguaiaretic Acid, Salt, and Temperature of Storage on the Stability of Fat and Fat-Soluble Vitamins in Cream and Butter," *J. Dairy Science*, 32(7):679-87, 1949.

Burger and Schumm, "Detection of a Minor contributor in a DNA Sample Mixture from Human Milk," *International Congress Series*, 1288:547-549, 2006.

Hartmann, B.T., et al. "Best Practice Guidelines for the Operation of a Donor Human Milk Bank in an Australian NICU," *Early Human Devel.* 83:667-673, 2007.

METHOD OF PRODUCING NUTRITIONAL PRODUCTS FROM HUMAN MILK TISSUE AND COMPOSITIONS THEREOF

CROSS-REFERENCE TO RELATED APPLICATIONS

This application is a Divisional Application of U.S. application Ser. No. 11/012,611 filed Dec. 14, 2004 now abandoned which is a continuation of U.S. application Ser. No. 10/144,325 filed May 13, 2002 now abandoned which claims priority to U.S. Provisional Patent Application Ser. No. 60/290,823 filed May 14, 2001.

FIELD OF THE INVENTION

The present invention relates to biopharmaceutical and nutritional products obtained from human milk and mammary gland secretions. More particularly, the present invention relates to methods of isolating, storing, transferring, processing, packaging and delivering pharmaceutical and nutritional formulations comprising cells and tissues of human milk, fractionated human milk components and specifically reunited components of human milk. One embodiment of the present invention relates to improving the nutrition of low birth weight infants. Another embodiment of the present invention relates to a novel type of immunoglobulin useful in treating disorders, such as, for example, cancer, immune disorders, gastrointestinal disorders, nutritional disorders and metabolic disorders.

BACKGROUND OF THE INVENTION

The lack of a standardized source of human milk, available for research purposes, has seriously hampered scientific investigation of human milk as well as the majority of the nearly 4,000 unique, species-specific milks. Accordingly, it would be desirable to provide a standardized source of human milk that can be modified to reflect the various stages of lactation and various immune responses.

Although the presence of immunoglobulins in human milk has been acknowledged for a number of years, the specific role and function of each of the human milk immunoglobulins and their subclasses has been poorly understood. For the patient of any age suffering from an immune disorder, the worldwide gamma globulin shortage is impacting care to such a degree that some patients are unable to obtain treatment. Purified immunoglobulins from human milk hold the potential for a solution for this worldwide shortage. Accordingly, it would be desirable to provide formulations comprising higher levels of immunoglobulins isolated from human milk, as well as methods to deliver these formulations to patients.

It has been known for a long time by physicians, scientists and nutritionists that the best food or nutrition supplied to an infant is its own mother's milk, i.e., fresh human milk. Recent research has indicated that "species-specific" milk plays a significant role in disease prevention and the severity of disease when the infant does become ill. Until recently, the reasons behind the superiority of species-specific milk were not well understood, nor were the various components and the roles they play in development and disease prevention. It is recognized, however, that many situations arise wherein the infant cannot obtain its mother's milk and as a result a suitable replacement is desired. Artificial baby milks, predominantly based on cow's milk, have been prepared and used to nourish an infant but there is increasing evidence that infants fed artificial baby milks suffer long-term ill consequences. It has been suggested that the exposure of an infant to any foreign proteins, such as the bovine protein, during the first few days of life will increase the infant's chance of becoming afflicted with juvenile diabetes. Other ill effects include allergies, lowered immunity, gastrointestinal disorders, respiratory disease and other associated etiology. Although much effort has been made to improve synthetic infant milk formulas, attempting to make them more closely simulate mother's milk, the presence of living organisms and other "species-specific" cells that act in a way to trigger other disease preventing mechanisms in the infant, these efforts have proven futile.

According to Jenness and Sloan, human milk contains three major groups of constituents that carry strong "species-specific" and "organ-specific" missions: (1) constituents specific to both organ and species, including proteins and lipids; (2) constituents specific to organ but not species, including lactose; and (3) constituents specific to species but not to organ, including albumin and some immunoglobulins.

Human milk is not a uniform body fluid; instead, it is a secretion from the mammary gland of constantly changing composition. In nature, the composition of human milk changes not only from day to day, but also throughout the course of a single day. While the reasons and outcome of these changes are not fully understood, it is intuitive to believe that these changes benefit the species and that substantial advantages may be gained for the infant who is provided an opportunity to reap the benefits of a modified formulation of 100% human milk. Accordingly, it would be desirable to provide formulations comprising human milk proteins as nutritional supplements and therapeutics for patients in need of gamma globulin therapy.

SUMMARY OF THE INVENTION

Compositions containing 100% human milk proteins, including the so-called host resistance factors (HRF) of human milk, as well as other nutrients, living cells, and components are useful when employed to enhance and improve outcomes for babies and children who are not able to obtain human milk from their mothers (or cannot obtain enough mother's milk or mother's milk in the formulation needed due to immunodeficiency of the mother) as well as other patients (including adults) suffering from immune disorders, nutritional disorders and other diseases and dietary challenges.

The sequential administration of many of the human milk constituents provides substantial value to the recipient because of metabolic and catabolic processes. It is at the core of the present invention to utilize such human milk constituents, in their processed form, in such a sequential fashion as to provoke the same type of chain reaction in the body. With this concept, the pairing of the processed milk tissue with the sequential and differentiated delivery methods, patients may enjoy a new type of preventative and therapeutic medicine. Because human milk immunoglobulins are specifically targeted to many diseases of the newborn, as well as the protective functions of the mucus membranes of the newborn's body, and contain higher levels of IgA, IgD, IgM and IgE, the term "panoglobulin" or "lactapanoglobulin" has been coined for this newly identified formulation. In addition to fighting immune disorders with a human-milk origin panaglobulin, patients preparing for surgery, chemotherapy, radiation or other "currently accepted, but destructive" therapies, may enjoy preliminary therapies that may mitigate the ill effects of their upcoming procedure. In the same fashion, the constantly changing nature of species-specific milk allows for the inclusion of the mammary gland as a laboratory of sorts, seeking not to simply initiate and artificially replicate structures like antibodies and proteins, but instead, to produce a bonafide human-produced fluid that can be isolated, processed and delivered for a highly targeted use against disease.

One embodiment of the present invention provides a nutritional formulation of isolated human milk containing protective human milk proteins or host resistance factors of human milk suitable for infant consumption which can be directly administered to an infant.

Another embodiment of the present invention provides a method of isolating human milk comprising the steps of collecting a sample of human milk from a donor in a collection device, storing the sample of milk obtained from the donor, and processing the milk sample by conducting a nutritional analysis on the milk sample; fortifying the sample with heat-resistant nutrients, pasteurizing the sample; fortifying the pasteurized sample with heat-sensitive nutrients and testing the sample to ensure successful pasteurization.

Yet another embodiment of the present invention provides a system for delivering human milk to an infant. The system contains a feeding tube treated to minimize adherence of milk fat to the interior of the feeding tube; a heated sheath surrounding the feeding tube and an enteral pump removably mounted to a motorized platform.

DETAILED DESCRIPTION OF THE INVENTION

The present invention and the methods of obtaining and using the present invention will be described in detail after setting forth preliminary definitions.

DEFINITIONS

The following definitions are provided to facilitate understanding of certain terms used in the present invention.

As used herein, "human-milk" means any stage of human milk production including the production of breast secretions not associated with lactation. These stages include, but are not limited to, colostrums, transitional milk and mature milk.

As used herein, "species-specific milk" means any milk that would be processed or formulated to provide an advantage of any kind to its own offspring.

As used herein, "second-best species-specific milk" means any milk that would be processed or formulated to provide a "close second" to its own species-specific milk resulting in better outcomes than using the standard bovine or soy based milk replacer.

The present invention describes a method that includes multiple steps and processes to harvest or isolate, store, transfer, process, package and deliver a variety of pharmaceutical and nutritional formulations containing cells and tissues comprising 100% human milk tissue, fractionated human milk tissue components and specifically reunited compounds, as well as novel methods and procedures to affect levels of such fractionated human milk tissue components, isolate them from raw human milk and deliver them through various methods including (but not limited to) ingestion, inhalation, intranasal administration, eye drops, ear drops, enema, douche, lavage, transdermally, rectally, intravenously, intramuscularly injection, direct injection, direct topical application, ng tube and jg tube.

Additionally, these formulations may be delivered through any of these methods, but when delivered, the present invention describes a sequence of delivery by which certain components or compounds will catabolize to create optimum conditions for the sequential delivery of an additional compound. For instance, if the formulation is nutritionally focused, the present invention provides a formulation that is specifically delivered in the morning, with a different formulation delivered in the afternoon and evening.

Little is understood at this time, as to why the formulation of mammalian milk evolves throughout the day. The present invention is directed to a method by which this differentiation is preferred and would create an improved outcome for the patient. Additionally, by any method, there may be an advantage to the "priming" of the patient by the delivery of certain processed human milk components, thereby eliciting a response in the patient's body that will improve outcomes when the next treatment in the sequence is followed. This sequential treatment concept would not be limited to the method of delivery. Instead, the present invention relates to the possibility that multiple delivery methods may actually trigger multiple advantageous responses in the patient, increasing the patients' chance of an improved outcome by coaxing the patient's system into active collaboration with the treatment method. This method simulates the natural processes of the mammalian immune system, which cannot be described as any one "silver bullet" but a series of complex communications between multiple cell structures and the offending pathogen.

The present invention relates to use of the disclosed methods and formulations from all mammalian species and is not limited to human beings. Additionally, the present invention encompasses all breast fluids as a potential source for harvesting milk and immune cells, as the mammary gland is a lymphoid organ, capable of producing immunoglobulins with or without accompanying lactation.

EXAMPLES

The following examples are intended to illustrate various embodiments of the present invention and are not to be construed as limiting the scope of the invention.

Example 1

Gamma Globulin Formulations

At the center of this invention, is the intent to solve the worldwide shortage of gamma globulin. The current source of gamma globulin is blood serum, and specifically IgG from human blood. The present invention discloses a prophetic inclination, based upon a 15-year study of human milk, that a new form of gammaglobulin referred to herein as "panaglobulin," "mammaglobulin" or "lactopanaglobulin" may replace the current gamma globulin. Because higher levels of IgA and IgM are present in human milk and colostrums, and a more diverse form of IgG as well, panaglobulins may provide protection beyond the scope of current gamma globulin therapy. Manipulation of the levels of immunoglobulins and their subclasses will result in formulations that are targeted at specific diseases or organ systems, making it possible to attack disease using nature's pharmaceutical laboratory, the mammary gland. Furthermore, milk donors who have weaned their babies or have initiated lactation without pregnancy could feasibly become human labs, becoming exposed through any method to mild strains of disease and producing the appropriate antibody in their milk. Since the breast is reactive to new exposures of pathogens, an array of new immunities can be produced to combat such diseases. Whether these types of donors could produce enough milk to become a primary source remains to be seen, but at least these donors could provide a human lab for biosynthesizing disease specific antibodies that could be replicated later using other methods.

Colostrum contains high levels of immunoglobulins, a vital defense mechanism that protects the newly born. sIgA provides immediate protection to the infant by lining the gastrointestinal system and providing a first defense against dangerous pathogens like *E. coli* and other devastating disease organisms. The invention discloses concentrated, processed sIgA for use as a prevention or therapeutic for gut disorders in patients of all ages. Potency levels will depend upon the severity of the disease, the general health of the patient and the cost of the processing.

Colostrum also contains IgG1, G2, G3, G4, IgM, IgD and trace amounts of other human origin immunoglobulins. All of these immunoglobulins function in a myriad of ways, targeting specific organs and disease states. Because the mammary gland is a lymphoid organ, it is capable of synthesizing immunoglobulins, especially the four IgG subclasses, making it possible to achieve a higher level of IgG subclasses in breast fluid than is present in human blood serum. This capability of the mammary gland is not limited to lactation, with measurable quantities of IgG present in breast ductal fluid from non-lactating women. Expressing ductal fluid may provide protective advantages to the donor, specifically the cleansing of the breast ductal system, as disclosed in a prior patent application by the inventor. This invention envisions breast fluid from non-lactating women as a potential source of human immunoglobulins. Current research cites a wide variety of volume and constituents present in colostrums, transitional milk and mature milk but little information exists. for the constituents present in the breast ductal fluid of non-lactating women. The present invention is directed to the ability to influence the volume and constituents of breast ductal fluid through dietary and pharmaceutical manipulation.

For nutritional and pharmaceutical applications, other valuable proteins contained in human milk include alpha-lactalbumin, beta-lactoglobulin, lactoferrin, serum albumin, lysozyme, and other proteins as well. Human milk has a higher proportion of alpha-lactalbumin and the host resistance factors or anti-microbial proteins of human milk, which include lactoferrin, lysozyme and secretory IgA, and account for 75% of the protein in human colostrum as compared with 39% in mature human milk. Additional human milk cells that provide substantial disease resistance in the newly born include lymphocytes, macrophages, and secretory IgA. Lactoferrin is present in relatively high amounts in human milk as is lysozyme and bifidus-stimulating factors. A major objective of this invention is to provide techniques and routines for improving the diet and feeding of infants, particularly very-low-birth-weight infants. By varying the levels of many of these species-specific milk constituents, the invention will result in a myriad of formulations specially suited to a wide variety of medical conditions.

Example 2

Collection of Donor Milk

U.S. Pat. No. 4,772,262, which is hereby incorporated by reference in its entirety, is directed to technology for milk removal. As disclosed in that patent, milk yields increase due to the sensory stimulus provided by the patented breast pump equipment. When milk yield increases, the formulation of milk including many of the valuable immunoglobulins also increase along with living cells, such as macrophages and lymphocytes. Lipids also increase and the mother's body responds to the stimulus by producing higher levels of prolactin that will trigger continuing milk supply and the secretion of additional nutrients into her milk.

Example 3

Storage of Donor Milk

Previous methods of collecting donor milk failed to recognize the importance of stimulation to the mammary gland as well as collection chambers designed for the anaerobic collection and transfer of donor milk. The invention describes such a method as part of its unique collection, storage and transfer system. Additionally, the preservation of milk components and nutrients is paramount to the success of the invention wherein harvesting of milk cells specific to the species will result in pharmaceutical and nutritional improvements in outcomes for the newly born or immune compromised patient. For that reason, it is important that the container in which the donor milk is stored, will preserve and protect these vital milk constituents from harm due to ultraviolet light and other damaging light rays. A UV coating or additive, applied to the collection bottle during the molding process or afterwards as an exterior coating or sheath will ensure that light degradation does not occur.

Finally, the design of the donor milk collection bottle should make it easy to draw off a sample of the donor milk without compromising the integrity of the milk sample. A proprietary design allows for a twist-turn valve to open and release a small amount of donor milk through a one-way valve into a test vial. The one-way valve prevents any bacteria or other pathogen from contaminating the milk sample. Additionally, a "tear down" design will allow frozen milk to be processed immediately, without the necessity of waiting for the milk to thaw. The tear down feature will provide an easy pull-tab that will strip the container from the frozen block of donor milk. The pull-tab will feature a tag on which a bar code is attached, so that during the tear down process, a "lot" numbering system will track the pooled milk back to their original donors.

Example 4

Transfer of Donor Milk

Novel designs for refrigerated transfer units utilizing alternative forms of energy and equipped with temperature indicator recorders ensure that the milk has been maintained under safe conditions. A programmable chip that records temperature variations as well as handling conditions (rough treatment can compromise milk quality by breaking cell walls), prevents the opening of the transfer case upon arrival at the processing plant. The milk is automatically rejected for quality issues and quarantined for further scrutiny. The transfer unit will contain a programmable chip that stores the contents, origin of contents, date shipped, date received, lot numbers and any other information required for quality control, regulatory or other reasons.

Example 5

Hospital Based Testing and Processing of "Mothers Own" Milk

The invention discloses a total quality control system that encompasses both routine and novel procedures and tests. For mothers wishing to provide their own milk for use specifically with their own baby, onsight testing will be done at the hospital. Standard donor screening will be done in accordance with current recommendations and accepted practices. In the present day, no routine testing is done in this case, and frequently the lack of testing causes consternation and concern in the physician with the end result being that babies are being routinely deprived of their mothers' milk. Upon questioning the areas of concern, several neonatologists indicated a concern for the presence of street drugs, disease pathogens and contaminants. To answer this concern, the invention includes a series of quick tests, designed to screen for the presence of the most common pathogens, drugs and contaminants. In order to provide the most efficient form of testing, a series of pumped milk is pooled, mixed and tested. A report is provided to the neonatologist and also placed in the infant's chart. The mothers' milk, intended for her own baby, is housed in the milk laboratory, under optimum storage conditions. Again, a temperature indicator on each container of milk ensures that milk has not been exposed to adverse conditions that may cause degradation or contamination. The temperature indicator is attached to a disposable cap that covers the container. In the event of adverse circumstances, the temperature indicator activates a locking mechanism and the milk is quarantined until further analysis can be done.

Example 6

Onsight (Hospital Based) Delivery Methods for Mothers Own Milk

Of special concern in high risk neonatal units, is the loss of milk fat through feeding tubes used to feed very-low-birth-weight, sick or pre-term infants. A special design for extruded tubing employs a method during the manufacturing process, that will eliminate the problem of fat sticking to the inside of the tubing. After extrusion, a heat treatment is applied to the inside of the tubing, via a "pull-through" rod. A heated element, coupled with an anti-static element, of sorts, eliminate the static charge while smoothing the "tackiness" of the interior tubing wall. Coupled with a heated sheath, used during the tube feeding to keep the flow of milk warm, the fat loss can be substantially decreased. A gentle rocking motion, created by a motorized platform on which the enteral pump sits, provides constant agitation and prevents the pumped milk from separating. Additional design features prevent the fat from clinging to the inside of the enteral syringe, in which the pumped milk is contained. A Teflon coating, or alternatively a silicone interior bag or collapsible bag made from a food safe polyvinyl may create additional solutions to this problem. Techniques associated with sequential feeding methods may also mitigate the problems associated with single feed method. By utilizing sequential feeds, the "foremilk" formulation (simulating the composition of the first milk a baby receives during a direct feeding from the breast), is administered. Low in fat, but high in volume, this feed usually takes more time than the higher fat "hindmilk" feed. The hindmilk feed can be then administered from a push syringe specially designed to conserve a large amount of the fat that normally would have stayed in the long tubing associated with the earlier feed.

Example 7

Plant Processing Methods

In the practices of this invention the human milk proteins, including the so-called host resistance factors (HRF) of human milk, are prepared by chemically fractionating the same using standard techniques, such as the Cohn method, from pooled donor milk. This method will form the basis for the extraction of the immunoglobulins for the ultimate purpose of purification and processing into nutritional, IV and injectable forms. The present invention discloses a completely closed system for processing.

Under this system, there is no opportunity for contamination. When the donor milk is received at the processing center, a representative sample from each donor lot is tested and cultured. The remaining samples in the lot are transferred to the freezer to hold until the cultures are read. From the strip-down phase to the spray drying of the final product, all processing occurs within a sealed system. After the lot has been cleared for processing, the frozen containers of milk are placed in an anaerobic chamber where the strip down of the bottle occurs. A filter prevents particles of stripped down plastic bottles from entering the processing system. The frozen chunks of donor milk are thawed, using a slow, continuous heat with a mild churning action. Once thawed, a nutritional analysis is performed to determine specific nutritional levels of the pooled donor milk. Depending upon the desired human milk formulation, the system automatically adjusts the formulation, using validated sources from human milk origin, if augmentation above the levels of the donor milk is desired. Fortification at this point is limited to nutrients that are not adversely affected by heat. As the fortification is being done, the milk is gently churned. The pasteurization process takes place, again, in the same closed system, using the Holder Method of 62.5 C for 20 minutes of 56C for 30 minutes. After pasteurization, the milk is cooled. Second stage fortification occurs at this point, with the addition of previously processed immunoglobulins, as well as selected, 100% screened human milk cells. After processing, final testing is done to determine that the pasteurization process has been successful.

The formulations and methods of the present invention may be embodied in other specific forms without departing from the teachings or essential characteristics of the invention. The described embodiments are therefore to be considered in all respects as illustrative and not restrictive. The scope of the present invention is defined in the following claims, rather than the previous description, and all changes that come within the meaning and range of equivalency of the claims are therefore to be embraced therein.

What is claimed is:

1. A method of making a pasteurized fortified human milk composition comprising the steps of:
    (a) collecting a sample of human milk from a donor in a collection device, wherein the collection device comprises a computer chip capable of recording temperature variations and handling conditions of the collection device;
    (b) storing the sample of human milk obtained from the donor; and
    (c) processing the sample of human milk obtained from the donor, wherein processing comprises the steps of
        (i) conducting a nutritional analysis on the sample of human milk;
        (ii) conducting a first fortification of the sample of human milk with heat-resistant nutrients from human milk;
        (iii) pasteurizing the sample of first fortified human milk;

(iv) conducting a second fortification of the sample of pasteurized first fortified human milk comprising addition of human immunoglobulins and/or human milk cells; and (v) testing the sample of fortified human milk to determine whether the pasteurization was successful, wherein such testing is done after step (c)(iii) or alternatively after step (c)(iv).

2. The method of claim 1, wherein the computer chip is further capable of recording the origin of the sample, contents of the collection device, volume of the collection device, shipping dates of the sample or lot number of the sample.

3. The method of claim 1, wherein the sample of human milk is frozen prior to the processing step.

4. The method of claim 1, wherein the collection device further comprises a twist-turn valve to open and release an amount of milk through a one-way valve into a test vial.

* * * * *